United States Patent
Rogosnitzky

(10) Patent No.: US 10,322,129 B2
(45) Date of Patent: Jun. 18, 2019

(54) THERAPEUTIC COMPOSITIONS CONTAINING DIPYRIDAMOLE, TREATMENT PACKS AND KITS INCLUDING SUCH COMPOSITIONS AND METHODS FOR PRODUCING SAME

(71) Applicant: O.D. Ocular Discovery Ltd., Rehovot (IL)

(72) Inventor: Moshe Rogosnitzky, Kiryat Ye'arim (IL)

(73) Assignee: O.D. Ocular Discovery Ltd., Rehovot (IL)

(*) Notice: Subject to any disclaimer, the term of this patent is extended or adjusted under 35 U.S.C. 154(b) by 0 days.

(21) Appl. No.: 15/577,800

(22) PCT Filed: Jun. 8, 2016

(86) PCT No.: PCT/IB2016/053370
§ 371 (c)(1),
(2) Date: Nov. 29, 2017

(87) PCT Pub. No.: WO2017/017540
PCT Pub. Date: Feb. 2, 2017

(65) Prior Publication Data
US 2018/0153893 A1 Jun. 7, 2018

Related U.S. Application Data

(60) Provisional application No. 62/172,660, filed on Jun. 8, 2015.

(51) Int. Cl.
*A61K 31/519* (2006.01)
*A61K 9/00* (2006.01)
*A61P 27/12* (2006.01)
*A61P 35/00* (2006.01)

(52) U.S. Cl.
CPC .......... *A61K 31/519* (2013.01); *A61K 9/0048* (2013.01); *A61P 27/12* (2018.01); *A61P 35/00* (2018.01)

(58) Field of Classification Search
CPC .................................................. A61K 31/519
USPC ...................................................... 514/262.1
See application file for complete search history.

(56) References Cited

U.S. PATENT DOCUMENTS

| | | |
|---|---|---|
| 3,031,450 A | 4/1962 | Fischer et al. |
| 4,382,953 A | 5/1983 | Ishii et al. |
| 4,912,092 A | 3/1990 | Gruber |
| 5,438,060 A | 8/1995 | Miyazaki et al. |
| 5,731,432 A | 3/1998 | Erion |
| 5,780,450 A | 7/1998 | Shade et al. |
| 6,300,328 B1 | 10/2001 | Klimko |
| 7,825,102 B2 | 11/2010 | Fishman et al. |
| 9,254,289 B2 | 2/2016 | Rogosnitzky |
| 9,901,580 B2 * | 2/2018 | Rogosnitzky ........ A61K 9/0048 |
| 2007/0010502 A1 | 1/2007 | Keith et al. |
| 2007/0225217 A1 | 9/2007 | Chappell et al. |
| 2010/0222369 A1 | 9/2010 | Fishman et al. |

FOREIGN PATENT DOCUMENTS

| | | |
|---|---|---|
| EP | 0011654 A1 | 6/1980 |
| EP | 0234854 B1 | 5/1991 |
| RU | 2008122978 A | 12/2009 |

OTHER PUBLICATIONS de la Cruz et al. , Pharmacol Toxicol, 1994, 75(5): 250-4.*
Rhodes et al., Lancet, 1995, 1(8430): 693.*
And Sharfman et al. , Int Oncol, 1995, 6(3):579-83.*
Rabinovich-Guillat et al., "Cationic Vectors in Ocular Drug Delivery", Journal of Drug Targeting, Oct.-Dec. 2004, pp. 623-633, vol. 12(9-10), Taylor&Francis.
Kumar et al., "Recent Challenges and Advances in Ophthalmic Drug Delivery System", The Pharma Journal 2012, pp. 1-15, vol. 1(4).
Ashton et al., "Formulation Influence on Conjunctival Penetration of Four Beta Blockers in the Pigmented Rabbit: A Comparison with Corneal Penetration", Pharmaceutical Research, 1991, pp. 1166-1174, vol. 8(9), Springer.
Abelson and Fink. "How to Handle BAK Talk", Rev Opthalmol. 2002, pp. 52-54, vol. 9 (12).
Farinelli et al. "Neuroprotective Actions of Dipyridamole on Cultured CNS Neurons", The Journal of Neurosicence, Jul. 15, 1998; pp. 5112-5123, vol. 18(14), Society for Neuroscience.
Chen et al., "Adenosine Rreceptors as Drug Targets—What are the Challenges?" Nature Reviews Drug Discovery, 2013, pp. 265-286, vol. 12, MacMillan.
Rogosnitzy et al., "Topical Dipyridamole for Treatment of Pterygium and Associated Dry Eye Symptoms: Analysis o User-Reported Outcomes", Mar. 2016, pp. 119, ARVO.
Wang and Ma, "Preparation and Clinical Application of Persantine Eye Drops, Chinese Journal of Hospital Pharmacy", Dec. 1997, pp. 138-139, vol. 17(3), Chinese language publication submitted together with English translation.
Search report in IL225279 dated Jun. 9, 2013 (original Hebrew + English translation).
Office Action in IL225279 dated Aug. 22, 2013 (original Hebrew + English translation).
Podos, "Effect of Dipyridamole on Prostaglandin Induced Ocular Hypertension in Rabbits" Invest. Ophthalmol. Visual Sci., Jun. 1979, pp. 646-648, vol. 8(16), Assoc. for Res. in in Vis. and Ophthal. Inc.
Mashovsky, "Drugs Impacting Blood Coagulation and Aggregation of the Thrombocyte", cited in "Medicinal Drugs" 16th edition, Publishing House "LLC RIA New Wave" Submitted for publication on Oct. 15, 2009, pp. 485-486, vol. 54, Editor: N.A. Litvina.

(Continued)

*Primary Examiner* — Rei Tsang Shiao
(74) *Attorney, Agent, or Firm* — Sinai Yarus; IPAttitude Ltd.

(57) ABSTRACT

A method comprising: (a) identifying a subject in need of treatment for cataract and/or nevus and/or tumor lesion; and (b) topically administering to the eye an amount of dipyridamole which is physiologically effective in treatment of cataract and/or nevus and/or melanoma.

18 Claims, No Drawings

(56) References Cited

OTHER PUBLICATIONS

International Search Report dated Jun. 19, 2014 in PCT/IB2014/059645.
Translation Validation for NPL citations 9 & 10 above.
De La Cruz Et al. (1994) Pharmacology and Toxicology 75:250-254.
SR/WO in PCT/IB2016/053370.
Internet site:http://pingueculaeyedrops.com/about-the-drops-html/ [attached copy doiwnoaded Jul. 27, 2017).
Skimming et al. "Effects of dipyridamole and adenosine infusions on ovine pulmonary and systemic circulations" Am J Physiol. Feb. 1997;272(2 Pt 2):H921-6 [Abstract].
Bijlstra et al. "Glyburide inhibits dipyridamole-induced forearm vasodilation but not adenosine-induced . . . " Clin Pharma. Ther. Mar. 2004;75(3):147-56 [Abstract].
Ghiardi et al. "The purine nucleoside adenosine . . . " Vision Research 1999, 39:2519.
Erion et. al., "Discovery of AMP mimetics . . . "J. Am Chem. Soc. 1999, 121:308.
Wilson & White "Intracoronary papaverine: an ideal coronaryvasodilator for studies of the coronarycirculation in conscious humans" Circulation (1986) 73(3):444-451.
Bal et al. "Mast cell density in pterygium, and its association with ultraviolet exposure in different climatic conditions . . . " Turkish Journal of Pathology 2006;22(1):11-16.
Deckert et al., Adenosine—an endogenous neuroprotective metabolite and neuromodulator, Journal of Neural Transmission, vol. 43 (suppl.), pp. 23-31 (1994)) [Abstract].
Hurmeric et al.(2013)"Single and multiple injections . . . "Clinical Ophthalmology 2013:7 467-473.
Rosenbaum et al. (1988) "Ocular inflammatory effects . . . " Amer. J. of Pathol. 133(1): 47-53.
Eye Wiki: Pinguecula (Oct. 17, 2017) American Academy of Ophthalmology (online publication).
Podos S.M. (1979) Invest. Opthalmol. Vis. Sci. 18(6):646-648.
Ocular Melanoma Foundation (2018) "About Ocular Melanoma" http://www.ocularmelanoma.org/about-om.
Amaro et al. (2017) "The Biology of Uveal Melanoma" Cancer Metastasis Rev 36:109-140.
FDA "Guidance for Industry and Reviewers" Dec. 2002.
Clark et al. Cancer research (1969) 29:705-726.

\* cited by examiner

THERAPEUTIC COMPOSITIONS CONTAINING DIPYRIDAMOLE, TREATMENT PACKS AND KITS INCLUDING SUCH COMPOSITIONS AND METHODS FOR PRODUCING SAME

RELATED APPLICATIONS

This application claims the benefit under 35 U.S.C. § 119(e) of provisional application U.S. 62/172,660 filed Jun. 8, 2015 and having the same title and inventor as the present application; which is fully incorporated herein by reference.

FIELD OF THE INVENTION

The various embodiments described are in the field of treatment nevus, melanoma and cataracts as well as products for use in such methods and methods of producing such products.

BACKGROUND

Ocular melanoma refers to two distinct diseases, uveal and conjunctival melanoma, which differ significantly in epidemiological aspects.

The average annual incidence of uveal and conjunctival melanoma is 5-6 and 0.6-0.8 per million people, respectively. Approximately 6679-7095 uveal and 1381-1618 conjunctival melanomas are diagnosed annually, and for each new patient at least 13-15 survivors are alive.

The incidence of ocular melanoma varies widely according to age, ethnicity and latitude. Most new cases are diagnosed between 45 and 80 years of age. Non-Hispanic white Caucasians have the highest incidence of uveal and conjunctival melanoma, 5.5-6.0 and 0.5-0.8 per million, respectively. The corresponding incidences are lowest in people of African and Asian origin, 0.2-0.4 and 0.15-0.18 per million, respectively.

The incidence of conjunctival melanoma increases with more UV radiation from 0.3 to 0.9 per million from high to low latitudes, whereas the reverse is true of uveal melanoma, which increases in incidence from 1.4 to 8.6 per million toward high latitudes.

Germline mutations of BAP1, which predisposes to several cancers, are an infrequent but important cause of familial uveal melanoma. The most important precursors of uveal melanoma are uveal nevi and congenital ocular and oculodermal melanocytosis, which carry a 1:400-1:500 lifetime risk of uveal melanoma. Primary acquired melanosis of the conjunctiva carries an even higher risk of conjunctival melanoma developing.

Conjunctival naevi are common lesions of the conjunctival epithelium and substantia propria. They are classified as either congenital or acquired, and usually develop during the first decade of life. Acquired naevi are typically located near the limbus, and may drape over the peripheral cornea. They rarely require excision, except where rapid growth or irritative symptoms are present. However they are cosmetically disfiguring.

"Inflamed naevi of puberty and young adulthood," as termed by Folberg and colleagues in their review of benign conjunctival melanocytic lesions, are conjunctival naevi that seem to be enlarging and are histologically associated with extensive inflammatory infiltrate.

Conjunctival melanocytic tumors comprise benign and malignant neoplasms.

Nevi are congenital benign melanocytic tumors that can be further classified into junctional, subepithelial, compound, and blue nevus as well as congenital melanocytosis. In the text, the term "nevus" refers to the most common form of nevi, the compound nevus (a nevus with a junctional and a subepithelial component).

Primary acquired melanosis (PAM) can either be regarded as benign (PAM without atypia) or represent a precancerous lesion (PAM with atypia), whereas a melanoma is per definition a malignant melanocytic tumor.

Nevi exhibit usually cysts (that can be detected on slit lamp examination and with sonography/anterior segment OCT) and are reported by the patient to exist for a long time (as they are often congenital).

Malignant melanomas can start as a nevus/freckle or arise as newly formed conjunctival pigmentation called primary acquired melanosis (PAM).

A simple biopsy can determine whether a pigmented conjunctival tumor is a nevus, primary acquired melanosis, or conjunctival melanoma. A biopsy is not a desirable procedure for anyone to undergo. It carries the risk of aggravating the growth of the lesion.

A nevus of the conjunctiva does not typically grow (except at puberty). They do not usually extend onto the cornea or develop large feeder blood vessels.

Pigmented conjunctival tumors that are raised, hypervascular, or extend onto the cornea are considered suspicious. Though suspicious conjunctival tumors can be biopsied after a first visit to the eye cancer specialist, close observation for evidence of growth (prior to biopsy) may also be recommended. Documented tumor growth is a strong indicator that biopsy should be performed.

A pigmented conjunctival nevus can be photographed and followed for evidence of growth prior to biopsy or excision. It is important to note that both benign and malignant tumors can grow (though malignant tumors will grow faster). Nevus are not expected to disappear spontaneously.

The predominant benign conjunctival melanocytic lesions are composed of a variety of nevi and melanosis that have a predilection for the perilimbal bulbar conjunctiva. Nevi are believed to be congenital lesions that are generally unilateral. They are usually first identified in early adulthood, they frequently develop cysts and become slightly elevated and may change in color and size. Dark brown melanotic pigmentation is normally observed in the conjunctiva, a condition referred to a racial melanosis, which is evident bilaterally form an early age in more pigmented races. This condition is usually caused by an excess production of melanin or hyperpigmentation by the melanocytes (forming an ephelis) or benign proliferation of melanocytes (forming a benign lentigo).

The terminology associated with melanosis is controversial, especially when melanosis is unilateral and acquired, in that case lesion can be a precursor of invasive melanoma. Some authors referred this unilateral acquired pigmentation as a precancerous melanosis, which in the past has led to an inappropriate aggressive therapy—frequently exenteration of the orbit (surgical excision of the orbital contents—the eyeglobe, muscles, and eyelids, too.) As a result, others have referred these lesions as benign acquired melanosis, but this terminology has caused concern that the malignant potential of this condition may be overlooked. Because these lesions may show variable histological findings, WHO proposed the term primary acquired melanosis (PAM) with or without atypia for these lesions.

Conjunctival melanoma is relatively rare condition, occurring only in ¹⁄₄₀th compared to choroidal melanoma and approximately 500 times less often than cutaneous melanoma. Its incidence is 0.2 to 0.8 per million in white population. Conjunctival melanoma is a potentially lethal neoplasm, with an average 10 year mortality rate of 30%. It is identified most frequently in the perilimbal interpalpebral bulbar conjunctiva with tumor masses located in the palpebral or fornical conjunctiva or caruncle, plica semilunaris or eyelid margins having a worse prognosis for survival. Conjunctival melanoma has no sexual predilection, and it is found predominantly in middle-aged adults. This disease occurs mainly in white population, with rare reports in black on other populations. Recent studies have indicated that the incidence of epibulbar melanoma is increasing similarly to cutaneous melanoma.

Conjunctival melanomas are malignant tumors of proliferating melanocytes that are derived from the neural crest. The conjunctiva is a mucous membrane covering the anterior half of the pericorneal globe (bulbar conjunctiva) and lining the posterior surface of the eyelids (palpebral conjunctiva) forming a fold in the superior and inferior fornices (forniceal conjunctiva). Since the conjunctival stroma (the substantia propria) contains blood vessels and lymphatic vessels, a malignancy that invades the subepithelial region has a potential for local and systemic metastases.

The aim of the treatment is to reduce the opportunity for spreading the tumor mass. Dissemination can be done by local extension and by spread into the regional lymphatic nodes (ipsilateral, preauricular and submandibular lymph nodes), which are the most common site for metastasis. The mortality rate is over 5%. When tumor arises from PAM, the mortality rate increases to 40%.

Other indicators of a poor prognosis are involvement of the palpebral conjunctiva, fornixal conjunctiva or caruncle, severe cellular atypia, invasion into deeper ocular tissues, greater than 5 mitotic figures per high-power field, lack of an induced inflammatory response.

A cataract is a clouding of the lens in the eye leading to a decrease in vision. Cataracts may affect one or both eyes. Often they develop slowly. Symptoms may include faded colors, blurry vision, halos around light, trouble with bright lights, and trouble seeing at night. This may result in trouble driving, reading, or recognizing faces. Poor vision may also result in an increased risk of falling and depression. Cataracts are the cause of half of blindness and 33% of visual impairment worldwide.

Cataracts are most commonly due to aging, but may also occur due to trauma, radiation exposure, be present from birth, or occur following eye surgery for other problems. Risk factors include diabetes, smoking tobacco, prolonged exposure to sunlight, and alcohol. Either clumps of protein or yellow-brown pigment may be deposited in the lens reducing the transmission of light to the retina at the back of the eye. Diagnosis is by an eye exam.

Clinical staging of senile cataract is based largely on the visual acuity of the patient, as follows:
Mature cataract—Patient cannot read better than 20/200 on the visual acuity chart
Immature cataract—Patient can distinguish letters at lines better than 20/200
Incipient cataract—Patient can still read at 20/20 but possesses a lens opacity as confirmed by slit lamp examination Prevention includes wearing sunglasses and not smoking. Early on the symptoms may be improved with eyeglasses. If this does not help surgery to remove the cloudy lens and replace it with an artificial lens is the only effective treatment. Surgery is only needed if the cataracts are causing problems. Surgery generally results in an improved quality of life. Cataract surgery is not easily available in many countries. This is especially true for women.

About 20 million people globally are blind due to cataracts. It is the cause of about 5% of blindness in the United States and nearly 60% of blindness in parts of Africa and South America. Blindness from cataracts occurs in about 10 to 40 per 100,000 children in the developing world and 1 to 4 per 100,000 children in the developed world. Cataracts become more common with age. About half of people in the United States have had cataracts by the age of 80.

SUMMARY OF THE INVENTION

One aspect of some embodiments of the invention relates to use of dipyridamole based compositions in treating ocular nevus, ocular melanoma and cataract and/or in formulation of medicaments for use in such treatments In some exemplary embodiments of the invention, dipyridamole applied topically to the eye (e.g. as drops, ointment or cream) alleviates symptoms of these conditions and reverses the nevi, tumor or cataract process.

As used in this specification and the accompanying claims the term "dipyridamole" includes pharmaceutically acceptable salts thereof.

In some exemplary embodiments of the invention there is provided method including: (a) identifying a subject in need of treatment for cataract and/or nevus and/or tumor lesion; and (b) topically administering to the eye an amount of dipyridamole which is physiologically effective in treatment of cataract and/or nevus and/or tumor lesion.

In some exemplary embodiments of the invention there is provided a method including: (a) surgically excising a cataract (e.g. by laser); and (b) topically administering to the eye an amount of dipyridamole which is physiologically effective in reducing the likelihood of cataract re-occurrence.

According to various exemplary embodiments of the two methods set forth above the dipyridamole is administered as part of a formulation as described hereinbelow.

Another aspect of some embodiments of the invention relates to treatment packs containing such dipyridamole compositions, packaging materials and instructions specifying a suitable dosage regimen for treatment of one or more specific disorders selected from the group of melanoma, nevus and cataracts.

Another aspect of some embodiments of the invention relates to dipyridamole with a concentration so dilute that it falls into the classification of a homeopathic preparation. Surprisingly, homeopathic concentrations of dipyridamole applied to the nevus, tumor lesions and cataracts provide real and significant therapeutic benefits as demonstrated in Examples presented hereinbelow. In some exemplary embodiments of the invention, the low concentrations contribute to a reduction in undesirable increases in nitric oxide levels and/or obviate a need for co-administration with benzisoselenazole or other NO inhibitors.

Such compositions and treatment indications would, inter alia, overcome the problems mentioned above associated with such ailments.

In some exemplary embodiments of the invention, dipyridamole is the main therapeutic agent in the composition and does not benefit from any synergistic effect with an additional therapeutic agent. In some embodiments, dipyridamole is the sole therapeutic agent in the composition.

In some embodiments, dipyridamole is provided in a composition without caffeine.

In some embodiments, dipyridamole is provided in a composition without corticosteroids.

In some embodiments, dipyridamole is provided in a composition without benzisoselenazoles (e.g. ebselen).

In some embodiments, the aggregate daily dosage of dipyridamole administered is 0.5 mg per day or less. Alternatively or additionally, in some embodiments the administration is topical.

In some embodiments, dipyridamole is used without concurrently or within 14 days administering amoxapine and/or sertraline and/or dipivefrin and/or prostaglandin E and/or rolipram.

In some embodiments, dipyridamole is used without HDAC inhibitors and/or additional anti-VEGF compounds and/or HMG-CoA reductase inhibitors such as statins and/or nitric oxide (NO) inhibitors.

In some embodiments dipyridamole is used with an agent that increases ocular surface permeability (e.g. benzalkonium chloride). In some embodiments use of such an agent contributes to an increase in ocular surface penetration by the dipyridamole.

It will be appreciated that the various aspects described above relate to solution of technical problems associated with treatment of treatment nevus, melanoma and cataracts.

Alternatively or additionally, it will be appreciated that the various aspects described above relate to solution of technical problems related to application of a known active ingredient to new clinical uses.

In some exemplary embodiments of the invention there is provided a composition including: (a) a physiologically effective amount of dipyridamole formulated for topical administration to a cataract, nevus or tumor lesion; and (b) a physiologically acceptable carrier. According to various exemplary embodiments of the invention the physiologically effective amount is different for cataract, nevus or tumor lesion. In some embodiments, the composition is formulated as a solution. In other exemplary embodiments of the invention, the composition is formulated as a cream or ointment. Alternatively or additionally, in some embodiments the physiologically effective amount of dipyridamole includes a concentration of at least about $10^{-6}$ molar (moles/liter). Alternatively or additionally, in some embodiments the composition includes 5 mg/ml; 4 mg/ml; 2 mg/ml; 1 mg/ml; 0.5 mg/ml; 0.25 mg/ml; 0.125 mg/ml; 0.0625 mg/ml; 0.03125 mg/ml; 0.2 mg/ml; 0.1 mg/ml; 0.01 mg/ml; 0.001 mg/ml; or lesser or intermediate concentrations of dipyridamole. Alternatively or additionally, in some embodiments the total daily dose of dipyridamole includes 1 mg/ml; 0.1 mg/ml; 0.01 mg/ml; 0.001 mg/ml; 0.0001 mg/ml; 0.00001 mg/ml; or lesser or intermediate amounts. Alternatively or additionally, in some embodiments the composition does not include a physiologically active concentration of any member of the group consisting of caffeine, a corticosteroid, a benzisoselenazole (e.g. ebselen), amoxapine, sertraline, dipivefrin, prostaglandin E, rolipram, an HDAC inhibitor, an additional anti-VEGF compound, and an HMG-CoA reductase inhibitor (e.g. a statin and/or nitric oxide (NO) inhibitor).

In some exemplary embodiments of the invention there is provided a treatment pack including: (a) multiple doses of a composition containing dipyridamole as an active ingredient; (b) packaging material; and (c) instructions for topical administration of the composition to a cataract, nevus or tumor lesion. According to various exemplary embodiments of the invention, the composition is formulated as a solution a cream or an ointment. Alternatively or additionally, in some embodiments the composition does not include a physiologically effective amount of any member of the group consisting of caffeine, a corticosteroid, a benzisoselenazole (e.g. ebselen), amoxapine, sertraline, dipivefrin, prostaglandin E, rolipram, an additional anti-VEGF compound, and an HMG-CoA reductase inhibitor (e.g. a statin and/or nitric oxide (NO) inhibitors) if the instructions are followed. Alternatively or additionally, in some embodiments the composition contains dipyridamole at a concentration of at least about $10^{-6}$ molar (moles/liter). Alternatively or additionally, in some embodiments the instructions specify administration of the composition to the eye(s) of a subject at least once every other day. Alternatively or additionally, in some embodiments the instructions specify a dosing regimen which leads to an aggregate daily dosage of dipyridamole of 0.5 mg per day or less. Alternatively or additionally, in some embodiments the treatment pack includes a single container for the multiple doses. Alternatively or additionally, in some embodiments the treatment pack includes multiple containers, each of the multiple containers containing a single dose of the multiple doses.

In some exemplary embodiments of the invention there is provided a method including: (a) adjusting the pH of a physiologically acceptable ophthalmologic solution to between about 5.5 and about 6.8; (b) dissolving dipyridamole in the solution at a concentration of 5 µg/ml to 200 µg/ml; and (c) sterilizing the resultant dipyridamole composition. In some exemplary embodiments of the invention, the method includes titrating the solution to achieve the pH equal to or below 6.7. Alternatively or additionally, in some embodiments the dissolving includes dissolving at a concentration of at least 85 µg/ml. Alternatively or additionally, in some embodiments the method includes packaging the sterilized dipyridamole composition in container configured to deliver drops to the eye. Alternatively or additionally, in some embodiments the method includes assembling a treatment pack including the container, packaging material and instructions for topical administration of the composition to the eye to treat an nevus and/or melanoma and/or cataracts in a subject in need thereof. Alternatively or additionally, in some embodiments the method includes advertising and promoting knowledge of this product to subjects in need thereof.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, actions or components without precluding the addition of one or more additional features, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

DETAILED DESCRIPTION OF EMBODIMENTS

Embodiments of the invention relate to treatment of nevus, melanoma and cataracts using dipyridamole and treatment packs for nevus, melanoma and cataracts including such dipyridamole and methods for producing such treatment packs.

Dipyridamole was found to be effective in treating ocular medical conditions such as nevus, nevi, melanoma and cataract when applied topically in liquid or cream formulations.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Technical Problem

Dipyridamole is practically insoluble in water (water solubility is 8.17 mg/L (Meylan, W M ET AL. (1996))), and very soluble in methanol. This creates a challenge for finding a suitable method for ocular application in which an aqueous solution delivered via single drops may contribute to patient compliance with a dosing regimen.

Exemplary Solution to Technical Problem

According to various exemplary embodiments of the invention compositions and/or treatment packs and/or methods of manufacture contribute to treatment of nevus and/or melanoma and/or cataract using dipyridamole. It was determined that by adjusting the pH of the aqueous solution to ~6.6 (6.5-6.7) or less, dipyridamole fully dissolves in the aqueous solution. The natural pH of tear fluid is 7.4; however, discomfort for the user will not be felt as long as the pH of the administered medication stays in the range of 6.6-7.8 (Sampath Kumar et al., "Recent Challenges and Advances in Ophthalmic Drug Delivery System," in *The Pharma Innovation*, Vol. 1, No. 4 (2012)). Others administer eye drops at a pH of 5.5 and find this pH to be optimal. Yet others administer eye drops with a pH as low as 3.0 and find this safe.

Other methods may be used to achieve water solubility such as ultrasonic mixing, or dissolving dipyridamole in methanol, chloroform, acetic acid, DMSO, or other carriers in which the dipyridamole is soluble, followed by adding water or saline, and then removing all or part of the carrier. Another method involves grinding the compound to a nanoparticle size prior to mixing in water/saline. It should be noted that when preparing more dilute formulations, less acidification was required. In some embodiments, acidification of the carrier to achieve solubility is achieved by addition of other acidulants commonly used in eye drops such as hydrochloric acid. Alternatively or additionally, in some embodiments sodium hydroxide is used to adjust pH. While aqueous solutions are one possibility for ocular instillation, preparing the dipyridamole in an oil or cream base is another method to overcome the aqueous solubility challenge.

Therefore, according to the some embodiments, there is provided for the first time a composition for use in treating as nevus and/or nevi and/or cataract and/or melanoma, the composition including: (a) an effective amount of a topically-administered dipyridamole. In some embodiments, the topically-administered dipyridamole is formulated as an ophthalmologic solution. In some embodiments, the effective amount corresponds to a concentration of at least about $10^{-6}$ molarity. In some embodiments, the effective amount corresponds to a concentration of at least about $10^{-5}$ molarity. Alternatively or additionally, in some embodiments the effective amount is based on a treatment administration of at least once every other day. These and further embodiments will be apparent from the detailed description and examples that follow.

Some exemplary embodiments of the invention relate to compositions for use in treating nevus and/or nevi and/or cataract and/or melanoma using dipyridamole. The aspects, uses, and advantages for such compositions may be better understood with reference to the accompanying description. The description is not to be taken in a limiting sense, but is made merely for the purpose of illustrating the general principles of the various embodiments of the invention. Exemplary embodiments of the present invention are detailed below in the following exemplary formulations and/or experimental examples.

It is indeed surprising that dipyridamole, and especially such a low concentration considered and homeopathic dilution is capable of treating what are considered to be intractable medical conditions. Nevus is often congenital and sometimes acquired, when it poses the greatest risk of converting into malignancy. Nevi don't spontaneously heal and are usually removed through a physical process such as surgery or cryoablation. Cataracts are typically treated surgically or by laser.

Exemplary Compositions

Some embodiments of the invention relate to a therapeutic composition for ophthalmologic use in treatment of nevus and/or nevi and/or cataract and/or melanoma. In some embodiments, the composition includes a physiologically effective amount of dipyridamole formulated for topical administration to the eye, particularly to the nevus, nevi, cataract or melanoma lesion and a physiologically acceptable carrier.

As used in this specification and the accompanying claims the term "physiologically acceptable carrier" indicates suitability for ocular administration. Exemplary carrier ingredients include, but are not limited to, water, saline solution, chelating agents (e.g. EDTA and/or EGTA), boric acid, preservatives, and pH adjusting agents (e.g. acids and/or bases).

In some embodiments, dipyridamole is the sole agent in the composition present in a therapeutically effective amount.

According to various exemplary embodiments of the invention the composition is formulated as a solution, cream or an ointment.

In some embodiments, the concentration of dipyridamole in the composition is of at least about $10^{-6}$ molar (moles/liter). Alternatively or additionally, in some embodiments the composition includes 5 mg/ml, 4 mg/ml, 3 mg/ml, 2 mg/ml, 1 mg/ml or lesser or intermediate amounts of dipyridamole.

According to various exemplary embodiments of the invention the composition does not include a physiologically active concentration of caffeine and/or a corticosteroid and/or a benzisoselenazole (e.g. ebselen) and/or amoxapine and/or sertraline and/or dipivefrin and/or prostaglandin E, and/or rolipram, and/or an HDAC inhibitor, and/or an additional anti-VEGF compound, and/or an HMG-CoA reductase inhibitor such as a statin and/or nitric oxide (NO) inhibitors.

Exemplary Treatment Packs

Some embodiments of the invention relate to a treatment pack including single or multiple doses of a composition containing dipyridamole as an active ingredient, packaging material and instructions for topical administration of the composition to the nevus, nevi, cataract or melanoma lesion. These treatments may be indicated either for humans or animal species such as dogs, cats, horses, sheep, livestock, chickens and others. According to various exemplary embodiments of the invention the packaging material is configured as a box and/or a blister pack and/or a bottle. In some embodiments, the bottle is a squeeze bottle with an integral dropper. In other exemplary embodiments of the invention, the bottle is provided with a separate dropper (e.g. fashioned as part of the cap). According to various exemplary embodiments of the invention the composition is provided as a solution and/or a cream and/or an ointment.

In some embodiments, the composition does not include a physiologically active concentration of caffeine and/or a corticosteroid and/or a benzisoselenazole (e.g. ebselen) and/or amoxapine and/or sertraline and/or dipivefrin and/or prostaglandin E, and/or rolipram, and/or an HDAC inhibitor, and/or an additional anti-VEGF compound, and/or an HMG-CoA reductase inhibitor such as a statin and/or nitric oxide (NO) inhibitor.

In some embodiments, dipyridamole is the sole agent in the composition present in a therapeutically effective amount.

In some embodiments, the composition contains dipyridamole at a concentration of at least about $10^{-6}$, or at least about $10^{-5}$, molar (moles/liter). Alternatively or additionally, in some embodiments the instructions specify administration of the composition to the eye(s) of a subject at least once every other day. According to various exemplary embodiments of the invention the instructions specify administration of the composition to the eye(s) of a subject once, twice, three, four or more times daily. In some embodiments, the composition and/or instructions are specific for treating children with these conditions.

In some embodiments, the instructions specify a dosing regimen which leads to an aggregate daily dosage of dipyridamole of 0.5 mg, 0.4 mg, 0.3 mg, 0.1 mg, 0.1 mg, 0.05 mg or 0.025 mg per day or lesser or intermediate amounts.

According to various exemplary embodiments of the invention the treatment pack includes a single container for the multiple doses and/or multiple containers, each of the multiple containers containing a single dose of the multiple doses.

Exemplary Methods

Some embodiments of the invention relate to a production method. In some embodiments, the method includes adjusting the pH of a physiologically acceptable ophthalmologic solution to between about 3 and about 6.8 and dissolving dipyridamole in the solution at a concentration of 5 µg/ml to 200 µg/ml and sterilizing the resultant dipyridamole composition. According to various exemplary embodiments of the invention sterilization is by filtration and/or heating.

In some embodiments, the method includes titrating the solution to achieve a pH of about 6.5. According to various exemplary embodiments of the invention titration is with citric acid and/or hydrochloric acid and/or sodium hydroxide and/or other acids and/or bases.

In some embodiments, the dissolving includes dissolving at a concentration of at least 85 µg/ml.

In some embodiments, the method includes packaging the sterilized dipyridamole composition in a container configured to deliver drops to the eye. According to various exemplary embodiments of the invention the container is configured as a squeeze bottle, as a bottle with a dropper incorporated into the cap or as single use packets. In some embodiments, the method includes assembling a treatment pack including the container, packaging material and instructions for topical administration of the composition to the nevus and/or nevi and/or cataract and/or melanoma. In some embodiments there is a "non-approved use" disclaimer. In some embodiments, the method includes administering the compound to the eye via injection. In some embodiments, the method includes administering the compound to the cataracts or to the lesions or nevi via injection. In some embodiments the method includes concentrations of injectable dipyridamole at concentrations below that of dipyridamole eye drops. In some embodiments, dipyridamole has never before been used if prepared at such a low concentration before.

Exemplary Dosages

According to various exemplary embodiments of the invention the daily dosage of dipyridamole administered to a subject is 2 µg, 5 µg, 10 µg, 15 µg, 20 µg, 25 µg, 50 µg, 75 µg, 100 µg, 200 µg, 300 µg, 400 µg, 500 µg, 600 µg, 750 µg, 1 mg, 1.5 mg, 1.75 mg, 2.0 mg, 2.5 or 5 mg or intermediate or lesser amounts. In cases where only 1 eye requires treatment, the dosage is halved. According to various exemplary embodiments of the invention the daily dosage is administered all at once, according to a twice daily regimen, a three times daily regimen or a four or more times daily regimen. In other exemplary embodiments of the invention, the dosing regimen is administered every other day.

In some embodiments, liquid formulations are administered as 1-2 drops (~50-100 µL)/eye at each administration.

In other exemplary embodiments of the invention, a cream or ointment formulation is administered at 0.05 to 0.3 ml/eye at each administration.

Exemplary Concentrations

According to various exemplary embodiments of the invention the concentration of dipyridamole in a composition administered to the eye is 2 µg, 3 µg, 4 µg, 5 µg, 10 µg, 15 µg, 25 µg, 50 µg, 100 µg, or 200 µg, 500 µg, 1000 µg or 2000 µg per ml. In some embodiments, cream or ointment formulations employ a lower concentration than liquid formulations.

It is expected that during the life of this patent many ophthalmologically acceptable carriers will be developed and the scope of the invention is intended to include all such new technologies a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Specifically, the invention has been described in the context of drops and ointments but might also be used as a cream or emulsion.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Exemplary Formulation A:

Dipyridamole eye drops were prepared as follows. Citric acid was mixed in 100 mL saline (0.9% w/v sodium chloride in sterile water) to obtain a pH of 6.4. 8.5 mg of dipyridamole was weighed, irradiated by UVB for 30 minutes for sterility, and diluted in the acidified 100 mL saline. This solution was then filtered through a 0.22 micron filter for sterilization, resulting in a solution containing 85 µg of dipyridamole per mL. Using a dropper, one drop (equivalent to approximately 0.05 mL) was applied to the eye.

Exemplary Formulation B:

Dipyridamole eye drops were prepared as follows. Citric acid was mixed in 100 mL saline (0.9% w/v sodium chloride in sterile water) to obtain a pH of 6.7. 4.25 mg of dipyridamole was weighed, irradiated by UVB for 30 minutes for sterility, and diluted in the 100 mL saline. This solution was then filtered through a 0.22 micron filter for sterilization, resulting in a solution containing 42.5 µg of dipyridamole per mL. Using a dropper, one drop (equivalent to approximately 0.05 mL) was applied to the eye.

Exemplary Formulation C:

Dipyridamole eye drops were prepared as follows. 8.5 mg of dipyridamole was weighed, irradiated by UVB for 30 minutes for sterility, and diluted in 100 mL of Ringer's Lactate. This solution was then filtered through a 0.22 micron filter for sterilization, resulting in a solution containing 8.5 µg of dipyridamole per mL. Using a dropper, one drop (equivalent to approximately 0.05 mL) was applied to the eye.

Exemplary Formulation D:

Dipyridamole eye drops were prepared as follows. 17 mg of dipyridamole was weighed, irradiated by UVB for 30 minutes for sterility, and diluted in 100 mL of Ringer's Lactate. This solution was then filtered through a 0.22 micron filter for sterilization, resulting in a solution containing 17 µg of dipyridamole per mL. Using a dropper, one drop (equivalent to approximately 0.05 mL) was applied to the eye.

Appropriate and accepted methodologies for measurement of improvement in the various described conditions were applied whenever possible in order to avoid relying only on patient-reported improvement. These methodologies included diagnosis by a physician and where appropriate physician assessment, slit lamp examination, and accepted forms of photography.

Example 1

Conjunctival Amelanocytic Nevus

A 5 year old boy was diagnosed with a Conjunctival Amelanocytic nevus by an ophthalmologist. Biopsy was not performed. The nevus was dark brown. It was not congenital and had appeared not long before diagnosis. Yellow cystic lesions developed and became very disfiguring so that within 4 years of diagnosis the boy was embarrassed to attend school. At age 11, initially one drop of Formulation A was applied to the eye twice daily. There was a very rapid improvement in appearance. Application continued for 4 months after which the nevus was no longer visible. The cystic elements continued to shrink in size—reducing by about 80% over baseline by this time. The boy continues treatment and is now socially accepted by his friends. Over the time of treatment, the patient switched to using Formula B, and then Formula C—eventually staying with that formula as it felt most comfortable to his eye. Sometimes the Formulation was applied once daily. Nevertheless it continued to show ongoing beneficial effect.

Example 2

Cataracts

Two human males in their mid 70's suffering from age related mature cataracts were treated with Formula C, with drops applied directly to the affected cataract twice daily. After a period of 3 months of treatment, the cataracts had reduced significantly and were classified as immature cataracts. The patients continue with ongoing application twice daily.

Example 3

Cataract

Two human males in their mid 60's suffering from age related mature cataracts were treated with Formula D, with drops applied directly to the affected cataract twice daily. After a period of 3.5 months of treatment, the cataracts had reduced significantly and were classified as immature cataracts. The patients continue with ongoing application twice daily.

Example 4

Cataract Recurrence Prevention

Four human males and two human females in their 60's and 70's suffering from age related mature cataracts, post surgical excision, were treated with Formula D, with drops applied directly to the affected eye once daily. After a period of 12 months of treatment, there was no recurrence visible.

Example 5

Melanoma

In a first experiment, a dog was diagnosed (with biopsy) as suffering from malignant melanoma in one eye. The dog's age and medical condition did not permit a surgical procedure as anesthesia was considered too dangerous. Formula B for two weeks at one drop twice daily, followed by Formula C for 4 months at one drop twice daily resulted in total disappearance of the lesion at assessment after 5 months of diagnosis.

A slight transient stinging was experienced by a third of the subjects upon application. Some subjects felt this more with the citric acid based formula rather than the Ringer's Lactate based formula.

The formulations described herein would be suitable for treatment in humans, both adult and pediatric, male and female, as well as in animal species including horses, dogs, cats, chickens, sheep and cattle.

It is recognized that higher concentrations as referred to in this application can also be used. The objective of the experiment was not to find the Maximum Tolerated Dose—as this is more likely to lead to side effects. Hence lower doses were investigated. It is very surprising that dipyridamole eye drops has the described effect, especially at such low concentrations. There is no obvious linkage between the described ocular medical conditions described herein, except when mentioned to the contrary, other than their presence in the front of the eye.

In all the cases described, detailed written instructions on use were provided to the subjects using them or to their caregiver/s.

In all the cases described above, the subjects were not suffering from any other ocular medical condition.

In all the cases described above, the subjects were diagnosed by an eye doctor or by a veterinarian.

The invention claimed is:

1. A method of treating cataract in a subject in need thereof comprising:
    topically administering to the eye an amount of dipyridamole which is physiologically effective in reduction of said cataract;
        wherein said physiologically effective amount of dipyridamole includes an aggregate daily dose less than or equal to 5 mg of dipyridamole.

2. A method of reducing the likelihood of cataract re-occurrence in a subject that has undergone surgical excision of a cataract comprising:
    topically administering to the eye an amount of dipyridamole which is physiologically effective in reducing the likelihood of cataract re-occurrence;
        wherein said physiologically effective amount of dipyridamole includes an aggregate daily dose less than or equal to 5 mg of dipyridamole.

3. A method of treating ocular nevus and/or ocular melanoma in a subject in need thereof comprising:
    topically administering to the eye a physiologically effective amount of dipyridamole;
    wherein said physiologically effective amount of dipyridamole includes an aggregate daily dose less than or equal to 5 mg of dipyridamole.

4. The method according to claim 3, wherein said subject is in need of treatment for ocular nevus.

5. The method according to claim 3, wherein said subject is in need of treatment for ocular melanoma.

6. The method according to claim 3, wherein said dipyridamole is formulated as a solution.

7. The method according to claim 3, wherein said dipyridamole is formulated as a cream or ointment.

8. The method according to claim 3, wherein said dipyridamole is the sole active ingredient administered.

9. The method according to claim 3, wherein said physiologically effective amount of dipyridamole includes an aggregate daily dose of ≤2.5 mg of dipyridamole.

10. The method according to claim 3, which does not include administering a physiologically active concentration of any member of the group consisting of caffeine, a corticosteroid, a benzisoselenazole (e.g. ebselen), amoxapine, sertraline, dipivefrin, prostaglandin E, rolipram, an HDAC inhibitor, an additional anti-VEGF compound, and an HMG-CoA reductase inhibitor (e.g. a statin and/or nitric oxide (NO) inhibitor).

11. The method according to claim 1, wherein said dipyridamole is formulated as a solution.

12. The method according to claim 1, wherein said dipyridamole is formulated as a cream or ointment.

13. The method according to claim 1, wherein said dipyridamole is the sole active ingredient administered.

14. The method according to claim 1, wherein said physiologically effective amount of dipyridamole includes an aggregate daily dose of ≤2.5 mg of dipyridamole.

15. The method according to claim 1, which does not include administering a physiologically active concentration of any member of the group consisting of caffeine, a corticosteroid, a benzisoselenazole (e.g. ebselen), amoxapine, sertraline, dipivefrin, prostaglandin E, rolipram, an HDAC inhibitor, an additional anti-VEGF compound, and an HMG-CoA reductase inhibitor (e.g. a statin and/or nitric oxide (NO) inhibitor).

16. The method according to claim 2, wherein said dipyridamole is formulated as a solution.

17. The method according to claim 2, wherein said dipyridamole is the sole active ingredient administered.

18. The method according to claim 2, wherein said physiologically effective amount of dipyridamole includes an aggregate daily dose of ≤2.5 mg of dipyridamole.

* * * * *